United States Patent [19]

Cramer et al.

[11] Patent Number: 5,723,596
[45] Date of Patent: Mar. 3, 1998

[54] EUROPEAN CORN BORER RESISTANCE GENETIC MARKERS

[75] Inventors: Jane H. Cramer, Madison; Jeanne Romero-Severson, Mazomainie; David West, Prescott, all of Wis.

[73] Assignee: Agrigenetics, L.P., San Diego, Calif.

[21] Appl. No.: 474,988

[22] Filed: Feb. 6, 1990

[51] Int. Cl.$^6$ .................. C12N 15/10; C12N 15/11; C12N 15/29; A01H 1/04

[52] U.S. Cl. .............. 536/24.3; 536/23.6; 435/172.3; 435/320.1; 435/418; 435/419; 435/6; 800/205; 800/200; 800/DIG. 56; 47/58; 47/DIG. 1

[58] Field of Search .................. 536/27, 23.6, 24.3; 47/58, DIG. 1; 435/6, 320.1, 172.3, 418, 419; 800/200, DIG. 56, 250, 205

[56] References Cited

PUBLICATIONS

Helentjaris et al. (1985) Plant Molecular Biology vol. 5: pp. 109–118.
Helentjaris et al. (1986) Theor. Appl. Genet. vol. 72: pp. 761–769.
Helentjaris et al. (1986) Maize Genetics Cooperation Newsletter 60: pp. 118–120.
Helentjaris (1987) Trends in Genetics vol. 3(8) pp. 217–221.
Feix et al. (1981) Chem. Abst 96:175325u.
Konstantinov et al. (1985) Chem. Abst 105:220061x and Grenetika, vol. 17(3) pp. 229–235.
Burr et al. (1983) In: Genetic Engineering Principals and Methods vol. 5, pp. 45–59. eds. Setlow and Hollaender.
Hoisington et al. (1987) Maize Genetics Cooperation Newsletter 61:49.
Helentjaris, T. et al. (1987) Trends in Genetics 3:217–221.
Hallauer, A.R. et al. (1981) In Plant Breeding II, Frey, K.J. (ed.) pp. 3–56.
Helentjaris, T. et al. (1985) Plant Mol. Biol. 5:109–118.
Evola, S.V. et al. (1986) Theor. Appl. Genet. 71:756–771.
Tanksley, S.D. et al. (1989(Biotechnology 7:257–264.
Paterson, A.H. et al. (1988) Nature 335:721–726.
Stuber, C.W. and Edwards, M.D. (1986) Proc. Ann. Corn and Sorghum Res. Conf. 41:70–83.
Edwards, M.D. et al. (1987) Genetics 116:113–125.
Soller, M. and Beckman, J.S. (1983) Theor. Appl. Genet. 67:25–33.
Romer-Severson, J. et al. (1989), "Use fo RFLPs for analysis of quantitative trait loci in maize", Current Communications in Molecular Biology, Helentjaris, and Burr (eds.), Cold Spring Harbor, pp. 97–102.
Halluer, A.R. and Miranda–Filh, J.B. (1988), "Quantitative genetics in maize breeding," 2nd ed., Iowa State University Press pp. 3–19.
Patch et al., USDA Tech. Bull. 823.
Schlosberg and Baker et al., J. Agr. Res. 77:137–156.
Ibrahim et al. (1954) Agron. J. 46:293–298.
Scott et al. (1964) Corp Science 4:603–606.
Scott et al. (1966) Crop Science 6:444–446.
Guthrie et al. (1971), Corn and Soghum Res. Conf. Proc. 26:165–179.
Klun et la. (1967) J. Econ. Entomol. 60:1529–1533.
Klun et al. (1970) Crop Science 10:87–90.
Russell et al. (1975) J. Econ. Entomol. 68:31–34.
Simcox and Weber (1983), Maize Genetics Newletter 57:107–108.
Onukogu et al. (1978) J. Econ. Entomol. 71:1–4.
Brindley et al. (1975) Ann. Rev. Entomol. 20:233–235.
Burr et al. (1988) Genetics 118:519–526.
Wehrhahn and Allard, R.W. (1965) Genetics 51:109–119.
Cowen, N.M. (1988) Theor. Appl. Genet. 75:857–862.

*Primary Examiner*—Douglas W. Robinson
*Attorney, Agent, or Firm*—Saliwanchik, Lloyd & Saliwanchik

[57] ABSTRACT

This invention provides means for identifying maize plants having resistance to the European corn borer (ECB). Restriction fragment length polymorphism (RFLP) marker probes which are genetically linked to loci which condition ECB resistance are provided. These probes are useful in breeding programs to identify ECB resistant gene types and thus allow the resistance traits to be introduced into non-resistant or less resistant corn varieties.

7 Claims, No Drawings

EUROPEAN CORN BORER RESISTANCE GENETIC MARKERS

BACKGROUND OF THE INVENTION

The process of improving plant varieties through breeding relies fundamentally on the ability to select those individuals in a population that possess the desired traits. Such selected individuals are then used as parental material for the production of subsequent populations upon which selection will again be exerted. In this way, the agronomic performance of a plant species is continually improved.

Historically, selection in plant breeding has been based on visual and metric assessments of plant characteristics which, taken together, define the plant's "phenotype." There are two significant limitations to this approach. A plant's phenotype is a product of its genotype and the environment to which it is exposed during growth. Often, environmental variation can overwhelm genetically-determined variation, so that the expressed phenotype may not accurately reflect the genotype. Secondly, many agronomically desirable characteristics, such as pest resistance, yield, or harvest index, may not have obvious visual manifestations, thus requiring time-consuming and often elaborate screening methodologies to uncover variation in field populations.

A linked-marker breeding program is an alternative approach to breeding directly for complex traits. Linkage between genes refers to the phenomenon in which genes on a chromosome show a measurable probability of being passed on together to individuals of the next generation. The closer two genes are to each other, the closer to one this probability becomes. In current practice, breeders attempt to identify easily detectable traits, such as flower color, seed coat appearance, or isozyme variants, that are linked to an agronomically desirable trait. The breeders then follow the agronomic trait in their segregating, breeding populations by following the segregation of the easily scorable trait. Unfortunately, there are very few of these relationships available.

The practical importance of genetic linkage to plant breeding is that it provides a time- and cost-efficient process for continual improvement of plant varieties. Several examples of the application of this genetic linkage involve the use of isozyme markers (see Tanksley, S. D. and Orton, T. (eds.) (1983) "Isozymes in Plant Genetics and Breeding, Part B"). A well-documented example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Normally, selection for the Mi gene directly in segregating populations presents several difficulties: 1) there can often be problems in maintaining proper infestation levels of the nematode during screening, 2) transplanting selected plants after screening risks field contamination with the nematode, 3) considerable time is required for pest damage to develop so that it can be scored, and 4) only two classes, resistance and susceptibility, can be distinguished. On the other hand, use of the Aps1 isozyme marker to indirectly select for the Mi gene has these advantages: 1) segregation in a population can be determined unequivocally with standard electrophoretic techniques, 2) the isozyme marker can be scored in seedling tissue, obviating the need to maintain plants to maturity, and 3) co-dominance of the isozyme marker alleles allows discrimination between homozygotes and heterozygotes (see Rick, C. M. in Tanksley and Orton, Ibid.).

The limitation to the use of such isozyme markers has been the small numbers of known markers relative to the size of the genome. This limitation has recently been overcome by the identification of a new class of molecular markers known as RFLPs (RFLP is an acronym for restriction fragment length polymorphism). The RFLP markers reveal variations in the DNA sequences which can be identified by digestion of the DNA with restriction enzymes. Restriction enzymes are bacterial endonucleases that bind to DNA at specific, short (usually 4-6 nucleotides) sequences and cleave the DNA at a precise site within that sequence. When this cleaved DNA is analyzed by electrophoretic and visualization techniques well-known in the field, a distinctive pattern of differently sized fragments is revealed for samples of DNA from genetically distinct individuals. Variations in the DNA sequence that alter the sites for restriction enzyme cleavage will result in a different pattern of restriction enzyme DNA fragments. Such variation is referred to as polymorphism. RFLPs have been shown to be stably inherited, co-dominant, genetic traits which segregate like Mendelian genes (Ruddle, F. H. (1981) Nature 294:115-120).

The power of RFLP markers is in part due to the fact that a practically limitless number of these markers are scattered throughout the genome (see Helentjaris et al. (1985) Plant Mol. Biol. 5:109-118 and Evola, S. V. (1986) Theor. Appl. Genet. 71:765-771). Furthermore, their detection does not rely on expression of the genetic material as a protein product (a requirement of isozyme markers), and it is not subject to tissue-specific or developmental regulation or to environmental variation. Yet, these are unique sequences of DNA whose basic character is conserved during sexual recombination. Taken together, these advantages have allowed the development of extensive linkage maps for several organisms. RFLP maps for several plant species are now available, including tomato and pepper (Tanksley, S. D. et al. (1988) Proc. Natl. Acad. Sci. USA 85:6419-6423), rice (McCouch, S. P. et al. (1988) Theor. Appl. Genet. 76:815-829), Arabidopsis (Chang, C. et al. (1988) Proc. Natl. Acad. Sci. USA 85:6856-6860), lettuce (Landry, B. S. et al. (1987) Genetics 116:331-337) and maize (Helentjaris, T. et al. (1987) Trends in Genetics 3:217-221).

While it is clear that there are significant advantages to using RFLP markers for the transfer/identification of traits determined by a single gene, the real power of the RFLP technology lies in its ability to identify markers for traits conditioned by several genetic loci. In agriculture, many economically important traits—such as yield, pest resistance, environmental tolerance—are the net result of the actions of multiple and independent genes, perhaps none of which can be individually isolated or examined due to limits in detection of variation. To manage such traits in a breeding program, plant geneticists have used selection schemes based on the statistical theories of quantitative genetics (see Falconer, D. S. (1960) Introduction to Quantitative Genetics). The centerpiece of plant breeding for quantitatively inherited traits is recurrent selection, which results in improvement of the mean of the population for desirable traits while maintaining some genetic diversity. Recurrent selection has provided a means of managing quantitative trait loci (QTLs) en masse, since it has not been possible previously to identify the underlying, individual genetic components that were responsible for the cumulative effect (Hallauer, A. R. (1981) in Plant Breeding II, Frey, K. J. (ed.), pp. 3-56).

Although statistical approaches have provided an estimate of the number of QTLs which contribute to the expression of several complex traits, the location of such loci is generally unknown. Therefore, a set of markers covering the entire genome is required to assure that all QTLs are identified. Such a requirement makes RFLP technology the only feasible tool for efficiently identifying and tracking all the relevant loci that contribute to a particular trait. Several theoretical discussions have been presented regarding the utility of marker loci for tracking QTLs (see Tanksley, S. D. et al. (1989) Biotechnology 7:257–264; Paterson, A. H. et al. (1988) Nature 335:721–726; Stuber, C. W. and Edwards, M. D. (1986) Proc. Ann. Corn and Sorghum Res. Conf. 41:70–83; Soller, M. and Beckman, J. S. (1983) Theor. Appl. Genet. 67:25–33). In addition, the identification of sets of markers for several QTL-determined traits have recently been reported. Martin, B. et al. (1989) Science 243:1725–1727, identified three RFLP markers in tomato that are linked to genetic loci involved in determining water use efficiency, a complex trait thought to be important in conferring drought tolerance. Edwards, M. D. et al. (1987) Genetics 116:113–125 identified marker loci associations to account for significant variation in several traits of maize that were widely recognized as involving QTLs. Paterson et al. (1988, Ibid.) identified sets of individual QTLs for three traits in tomato—fruit weight, soluble solids concentration, and pH—which were known to be controlled by several genes. Romero-Severson, J. et al. (1989), "Use of RFLPs for analysis of quantitative trait loci in maize," Current Communications in Molecular Biology, Helentjaris, T. and Burr, B. (eds.), Cold Spring Harbor, pp. 97–102 report a marker set for maize dwarf mosaic virus resistance that includes six QTLs.

Hallauer (1981), Ibid. has pointed out that "most evidence suggests that genes with additive effects and partial dominance are of primary importance for maize yield." Similarly, other traits that are under polygenic control have been shown to exhibit additive and partially dominant effects of individual QTLs. Once markers have been identified for the individual QTLs contributing to a particular trait, it is possible to assign relative contributions to each locus for the total variation associated with the trait. RFLP markers, given their distribution throughout the genome, permit such assessments.

It is important to emphasize that genetic variation is the only variation that can be consistently manipulated in a breeding program. Phenotypic scoring of variation within a population in the field is the result of genetic and environmental variation. Thus, it is critical that field experiments are properly designed and executed so that variation due to environmental factors can be quantified. RFLP marker technology will predict only that fraction of the observed phenotypic variation that is due to genetic factors.

Thus, the variation that can be accounted for by RFLP marker associations is limited by the heritability of the trait. Heritability refers to that percentage of variation in a trait that is due to genetic differences. It is exactly this RFLP-associated variation that will be useful in selecting potentially superior individuals. RFLP marker-based selection assures consistent advancement of the population despite variable and often unpredictable fluctuations in expression of a trait due to the environment (see Hallauer, A. R. and Miranda-Filho, J. B. (1988), "Quantitative genetics in maize breeding," 2nd ed., Iowa State University Press for a discussion of heritability and estimates of heritability for several traits in maize).

The potential application of RFLP technology to plant breeding is enhanced by the ability of breeders to develop optimal plant populations for mapping. In contrast to the limitations of the human population, where only families carrying an identifiable, negative factor (i.e., a disease) have been analyzed, plant geneticists are able to study the inheritance of positive, multigenic traits whose expression are often strongly affected by environment. Since breeders can develop the appropriate population structure for mapping a particular QTL, they can draw much stronger inferences about the underlying molecular basis for expression of the trait.

The present application identifies a set of loci that determine resistance to the European corn borer (*Ostrinia nubilalis* Hubner), a world-wide lepidopteran insect pest of maize (*Zea mays* L.). Since its introduction to the United States sometime between 1909 and 1914, the European corn borer (ECB) has become a major pest on corn crops throughout North America. In general, throughout the Corn Belt of the United States, yield losses to ECB infestations have been established at around 1–3%/borer/plant (Lynch, R. E. (1980) J. Econ. Entomol. 73:159–164). In popcorn, yield losses attributable to ECB on a popular variety grown in the Midwest (Iopop 12) ranged from 16 to 35% depending on the level of infestation (Jarvis, et al. (1986) J. Econ. Entomol. 79:764–768). Andrew and Carlson (1976) J. Am. Soc. Hort. Sci. 101:97–99) report that the ECB is a "serious insect pest on processing sweet corn in the Midwestern U.S." In addition to the direct losses in yield, there is an additional problem of increased contamination of corn products by aflatoxin-producing fungi when the ears are infested with ECB (McMillan et al. (1988) J. Entomol. Soc. 23:240–244). Aflatoxin is a potent carcinogen, and the world corn product is carefully monitored for its presence, with significant tonnage being destroyed if aflatoxin levels are above the accepted tolerances.

Currently, most commercial production relies on the use of insecticides to control this pest in maize. The ability to transfer resistance to this pest into elite varieties would be valuable to the world corn industry.

Much research has focused on the identification of genes for resistance to the ECB. This work has been complicated by the existence of two or more generations of the ECB during the corn growing season. In the Midwest Corn Belt of the United States, there are typically two generations of ECB. As described by Guthrie, W. D. (1971), Corn and Sorghum Res. Conf. Proceedings 26:165–179, the first generation of the ECB is deposited as eggs on the underside of the corn leaves when the plant is in the whorl stage. These eggs hatch, and the resulting first and following second instar larvae feed on the whorled leaves. The term instar refers to the larval growth stages between molts. As the plant grows out of the whorl stage, the third and fourth instar larvae feed mostly on sheath and collar tissue. The fifth instar larvae tunnel into the stalk and pupate. The first generation adults emerging from these pupae lay their eggs (i.e., the second generation) on the upper leaves of the plant as well as on the flag leaves and the husks of the ear. The first and second instar larvae of this second generation feed on recently-shed pollen that has accumulated in the axils of the leaves as well as on sheath, collar, ear shoot, husk and silk tissues. Subsequent instars feed exclusively within the stalk causing extensive damage. Thus, the developmental stage of the plant is quite different for the first generation ECB compared to the second (and any subsequent) generations of ECB. It is therefore not surprising that much of the literature on resistance of corn germplasm to the ECB distinguishes between resistance to the first and second "broods" (i.e., generations). As Russell et al. (1974) Crop Science 14:725–727 point out, the use of the terms first and second brood resistance is a matter of convenience. The significant difference lies in the different stages of plant growth that these two generations of the insect are presented with.

In studies on dent corn in 1942 by Patch et al., USDA Tech. Bull. 823, and on sweet corn in 1948 by Schlosberg and Baker, J. Agr. Res. 77:137–156, it was concluded that "multiple factors" were responsible for resistance to ECB. In 1954, Ibrahim (Agron. J. 4.6:293–298) used chromosomal interchange (C.I.) lines in concluding that resistance to the first generation of ECB was conditioned by at least three genetic loci. In 1964, Scott et al. (Crop Science 4:603–606) established that inheritance of resistance to the ECB was mainly due to additive genetic variance. The source of resistance in this study was the inbred CI31A. These researchers suggested that, due to the activity of several genes in conferring this trait, the best breeding approach would be a recurrent selection program, "assuming that the inheritance of resistance is the same in all sources of resistance, and studies are needed to verify this assumption." Since these early reports, several efforts at improving cultivar resistance to ECB have been made. Tseng et al. (1984) Crop Science 24:1129–1133 reported success in improving resistance to the first generation ECB through recurrent selection. Klenke et al. (1986) Crop Science 26:864–869 also evaluated the success of a recurrent selection program for ECB resistance, but in this study, increases in resistance in advanced cycles was associated with a decline in yielding ability. They reported "no yield advantage of this more resistant material under high [ECB] infestation levels."

Several researchers have attempted to determine the position of genes conditioning resistance to the ECB within the maize genome. The use of chromosome interchange (C.I.) lines allowed Ibrahim (Ibid.) to tentatively identify chromosomal locations for three loci: the long arm of chromosome 3, the long arm of chromosome 4, and the long arm of chromosome 5. The source of resistance in this study was Oh7, an inbred dent corn line. Scott et al. (1966) Crop Science 6:444–446 identified the following locations for the genes involved in this additive, or quantitative, resistance in CI31A: short arms of chromosomes 1, 2 and 4; and the long arms of chromosomes 4 and 6. Interestingly, this study also included an evaluation of another corn inbred showing resistance to ECB, B49. In addition to chromosomes 1, 2 and 4 being identified as containing genes for resistance to ECB in this cultivar (leading the authors to suggest that they are possibly allelic to those of CI31A), an additional locus was identified on chromosome 8. This result lends further support to the additive nature of the genetic factors conditioning resistance to the borer. These researchers concluded that their "results show that resistance is conditioned by a relatively large number of genes," and they suggested that "some method by which genes for resistance could be accumulated (i.e., mass selection, recurrent selection, etc.) would effectively obtain breeding material containing a high degree of resistance."

Overall, the research on chromosomal location of loci important in conditioning resistance to the ECB indicates that these loci are scattered throughout the maize genome. However, the identification of locations for genetic loci using chromosomal interchanges is superficial, since it only narrows the location to a particular chromosome or half-chromosome. RFLP mapping technology is a sweeping refinement, targeting a small, exact location within a particular chromosome. In addition, the polymorphism inherent in the RFLP technology allows the breeder to follow a particular allele in a segregating population. In contrast, studies of chromosomal interchanges only locate the loci of interest to a particular chromosome; they do not provide a means for manipulation of the loci.

It is important to recognize that resistance to the ECB is the outcome of a complex interaction between two living organisms. This interaction includes, but is not limited to, location of the host plant by the insect, egg deposition, egg hatching, larval feeding and maturation, and pupation. Mechanisms of resistance can affect any or all of these steps. Additionally, some resistance may actually reflect tolerance of the maize crop; that is, high yield may be sustained despite the occurrence of damage caused by the ECB. In maize breeding, several cultivars have been identified and utilized as sources of resistance to the ECB. Despite the attempts to estimate the relatedness of different sources of resistance using information from chromosome interchange lines as described above, it has not been possible to clearly determine what loci, if any, are common among these known sources of resistance and/or tolerance. Given the complicated nature of the interaction and the knowledge that many genes are involved in determining resistance, the presence of the same locus or loci in otherwise unrelated lines would not be unexpected. It is also possible that resistance expressed by one cultivar may be a subset of the genes for resistance expressed by another cultivar. Only through the use of RFLP mapping technology (and/or the isolation of the actual genes involved) is it possible to determine the relatedness of the resistances conditioned by various maize cultivars.

Despite the understanding of the biology of the interaction and the existence of resistant cultivars, the biological basis for resistance for most of these cultivars remains unknown. Guthrie (1971), Corn and Sorghum Res. Conf. Proceedings 26:165–179 summarized the knowledge of the biological basis of at least one type of resistance in maize to the ECB. In his studies, resistance to the first brood is expressed as larval mortality within the first several days following egg hatch. This mortality is due to a high degree of antibiosis in the leaf tissue; thus in this case, first brood resistance is defined as leaf feeding resistance. Early researchers, in attempting to find the causative agent in the leaf tissue that was responsible for the antibiosis, found an association of this activity with the concentration of 2,4-dihydroxy-7-methoxy (2H)-1,4-benzoxazin-3 (4H)-one, referred to by the acronym DIMBOA (Klun et al. (1967) J. Econ. Entomol. 60:1529–1533). Further research by these workers established a significant correlation between the concentration of DIMBOA in the leaf-whorl tissue and first brood resistance, leading them to suggest the use of DIMBOA content as a selection tool for first brood resistance to ECB (Klun et al. (1970) Crop Sci. 10:87–90). Russell et al. (1975) J. Econ. Entomol. 68:31–34 tested this suggestion by comparing the effectiveness of two selection methods—DIMBOA content and visual evaluation for leaf-feeding (i.e., first brood) resistance—in developing borer-resistant maize populations from a cross of WF9 (borer-susceptible, low DIMBOA) and CI31A (borer-resistant, high DIMBOA). They found that a selection scheme based on DIMBOA content resulted in inbred lines with high resistance to first brood ECB. However, their data also indicated that there are other genetic factors, unrelated to the DIMBOA content, that contribute resistance to the ECB. These results once again illustrate the additive nature of the genetic loci involved in conditioning resistance to ECB. As these researchers indicated, due to additive gene action, progenies "lower in DIMBOA at the $F_3$ level could become equal to CI31A (in resistance to the borer) in subsequent generations if selection were effective in fixing favorable alleles in the homozygous state." The Bx factor which determines the occurrence of cyclic hydroxamates (DIMBOA) has been located on the short arm of chromosome 4. (Simcox and Weber (1983), Maize Genetics Newsletter, 57:107–108).

As described above, the larval instars of the second brood of the borer feed extensively on sheath and collar tissue.

According to Onukogu et al. (1978) J. Econ. Entomol. 71:1–4), data available through 1978 indicated that genes determining resistance to leaf feeding (i.e., first brood resistance) generally did not play a significant role in conferring resistance to sheath and collar feeding (i.e., second brood resistance). Still, their analysis of the location of genes for resistance to the second brood identified three of the same chromosome arms identified by Scott et al. (1966) as containing genes for resistance to the first brood, i.e., the long arms of chromosomes 4, 8 and the short arm of chromosome 1. It is thus quite possible that linkage may be detected for the genetic factors determining these two resistances in certain maize populations.

The existence of multiple genetic loci conditioning resistance to first and second generation ECB in maize creates a formidable problem for breeders in transferring recognized resistance in certain inbred lines to other, elite genotypes. The traditional process of screening for resistance by field infestation has several inadequacies. Production of large numbers of borer eggs for infestation is a costly and involved exercise. Additionally, levels of damage and infestation are strongly affected by environmental variations, necessitating extensive replication of experiments at several locations. With multiple loci to be recovered in the desired progeny, the number of individuals that must be screened, with proper replication, is extremely large (see review by Brindley, et al. (1975) Ann. Rev. Entomol. 20:233–235 for a discussion of screening procedures and difficulties).

The present invention will alleviate these difficulties by providing a set of markers that are easily scored in segregating populations in a nondestructive manner without the need for artificial infestation. This invention also substantially reduces the risk of losing one or more of the QTLs associated with ECB resistance during a recurrent selection program.

SUMMARY OF THE INVENTION

A set of four RFLP marker probes, designated c94 on chromosome 4, BNL5.46 on chromosome 4 and p1000 or c595 on chromosome 9, are provided which are genetically linked to loci that condition resistance to the European corn borer. These probes are referred to as "primary probes" or "primary markers" herein. Three segments of the maize genome are also claimed. These segments contain the genetic loci linked to the RFLP markers described above, and each segment is defined as the chromosomal DNA fragment between two flanking probes. The following flanking probes are provided: r115, r109, c39, r90, r92, and UMC31. The following probes comprise new compositions of matter:

The probes useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the probes are as follows:

| Probe | Repository No. | Deposit Date |
|---|---|---|
| c39 | NRRL B-21844 | September 30, 1997 |
| c94 | NRRL B-21845 | September 30, 1997 |
| c595 | NRRL B-21846 | September 30, 1997 |
| p1000 | NRRL B-21847 | September 30, 1997 |
| r90 | NRRL B-21848 | September 30, 1997 |
| r92 | NRRL B-21849 | September 30, 1997 |

-continued

| Probe | Repository No. | Deposit Date |
|---|---|---|
| r109 | NRRL B-21850 | September 30, 1997 |
| r115 | NRRL B-21851 | September 30, 1997 |

The probes were deposited under conditions that assure that access will be available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject probes will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the probes. The depositor acknowledges the duty to replace the deposit(s) should the depository be unable to furnish a sample when requested, due to the condition of a deposit. All restrictions on the availability to the public of the subject probes will be irrevocably removed upon the granting of a patent disclosing them. BNL5.46 and UMC31 are clones developed in the public sector whose linkage with European corn borer resistance was discovered by the present inventors.

These probes are useful in breeding programs to identify European corn borer resistant gene types and to breed this trait into maize varieties, including sweet corn and popcorn.

Definitions

The term "clone" as used herein refers to a cloned segment of maize chromosomal DNA or a complementary DNA (cDNA) synthesized from maize mRNA. The term "probe" as used herein is a nucleic acid sequence corresponding to a particular maize clone that is derived or developed by any one or more of the following methods:

(1) the "probe" may be an exact DNA copy of the maize DNA clone.

(2) the "probe" may be a DNA subclone of the maize clone.

(3) the probe may contain all or a portion of the DNA sequence of the original maize clone and additional, contiguous DNA from the maize genome. This is termed a "contiguous probe." This additional DNA is referred to as "upstream" or "downstream" of the original maize clone, depending on whether the contiguous DNA from the maize chromosome is on the 5' or the 3' side of the original DNA clone, as conventionally understood. It is preferable that the contiguous probe sequence is located between the original clone and the ECB locus on the maize genome. As is recognized by those skilled in the art, the process of obtaining contiguous clones can be repeated indefinitely, thereby identifying additional probes along the maize chromosome. For the purposes of this invention, all above-described probes are equivalent to the original probes named herein.

(4) the "probe" may contain a DNA sequence which is not contiguous to that of the original maize clone; this probe is a "noncontiguous probe." It is understood that the sequence of the noncontiguous probe is located sufficiently close to the sequence of the original clone on the maize genome so that the noncontiguous probe gives experimental results which are functionally equivalent to those obtained with the original clone as probe, that is it is genetically linked to the same ECB resistance locus.

(5) the "probe" may be a nucleic acid sequence which is substantially homologous (preferably at least about 85%) to said maize clone. Such homology is determined by the use of appropriate hybridization conditions, examples of which are described in "Nucleic Acid Hybridization" (1985) Hames, B. D. and Higgins, S. J. (eds.), IRL Press, Oxford and are well-known to those skilled in the art. Such a nucleic acid sequence can be derived from libraries of maize DNA using hybridization techniques. Alternatively, such a probe can be synthesized chemically once the sequence of the maize clone is known. Sequencing of maize clones is a routine practice of those skilled in the art.

(6) the "probe" may be an RNA version of any of the types of probes described above. RNA probes can be synthesized by means known in the art, using the DNA version of the probe or clone.

In all the types of "probes" described above, there may be included additional nucleic acid sequences, such as promoter, transcription signal, and vector sequences.

Any of the above probes can be used to define the maize chromosomal segments conditioning resistance to the ECB, and chromosomal segments thus identified are equivalent to the chromosomal segments defined by the probes named in this invention and thus are within the scope of this invention.

The terms "trait" and "phenotype" are used interchangeably herein. For the purposes of this invention, a "trait" can be a visible characteristic, such as ECB resistance and/or tolerance, high yielding ability, or eliteness. Additionally, a "trait" can be an enzymatic factor or the existence of a particular RFLP upon digestion of the DNA with a restriction enzyme followed by hybridization to a probe or clone.

A "locus" is a position on the genome that corresponds to a measurable trait. An RFLP locus is defined by a probe that hybridizes to DNA contained within the locus. All probes which are associated with ECB resistance by the "leaps and bounds" statistical analysis described herein are considered to define the locus.

A "marker" is a segment of DNA for which recombination frequencies with other DNA segments or observable traits have been determined. In addition to RFLP markers, several isozyme and phenotypic markers are known to the art, such as Adh2 and Su1, and these can be useful in the practice of this invention.

A "marker allele" refers to the version of the marker that is present in a particular individual.

DETAILED DESCRIPTION OF THE INVENTION

A set of nucleic acid probes are provided that hybridize to plant genomic sequences linked to genes that determine resistance to the European corn borer. This resistance is expressed at the whorled-leaf stage of maize plant development and is commonly referred to as "first brood" resistance. In the preferred embodiment, these probes are DNA or RNA probes that have the following designations: c94, BNL5.46, p1000 and c595. These probes are referred to herein as "primary probes," and they are tightly linked to genetic loci in the donor parent that condition resistance to the ECB, referred to herein as "primary loci." p1000 and c595 are adjacent to each other and separated by 9 cm on a maize chromosome. Either can substitute for the other as a primary probe, suggesting that they are approximately equidistant from the actual genetic locus and define the DNA segment containing it.

A further set of "flanking probes" are provided to enable detection of maize DNA segments. As used herein, there are two types of flanking loci that are marked by flanking probes which are distinguishable based on the statistical analyses described herein. One type of flanking locus, when present as the donor parent allele, shows an association with the desired phenotypic trait. However, this association is weaker in statistical terms than the association of the primary locus with the trait. The association of this type of flanking locus with the primary locus reflects genetic linkage of these loci. In segregating populations or in a group of recombinant inbred (RI) lines, individuals can be identified that carry the donor parent alleles of a primary locus as well as two flanking loci (on both sides of the primary locus). If the flanking loci are of the type described above, it can be unequivocally stated that the actual gene contributing to the desired trait lies between the two flanking loci and is located closer to the primary locus than to either flanking locus.

A second type of flanking locus shows little or no statistical association with the phenotypic trait regardless of whether it is present as the donor or recipient parent allele. Again, in segregating populations or in a group of RI lines, individuals can be identified that carry the donor parent alleles of a primary locus as well as two flanking loci. If the flanking loci are of this second type, it can again be stated unequivocally that the actual gene contribution to the trait lies between these two flanking loci and is considerably closer to the primary locus than either flanking locus. Additionally, it is known that some minimal amount of extraneous DNA (i.e., chromosomal DNA not associated with the trait) from the donor parent is also present in such individuals.

Use of both types of flanking probes, either solely or in combination, allows breeders to transfer the minimal segment(s) of donor parent DNA to the elite recipient parent that unequivocally contains the desired genes contributing to the trait.

In a preferred embodiment, the probes defining the DNA segments containing trait loci are DNA or RNA probes synthesized from cloned DNA segments of maize that have the following designations: r115, r109 or c39 (r109 is equivalent to c39), r90, r92, UMC31. In a more preferred embodiment, r90 is replaced by p1000 and r92 is replaced by c595. Although p1000 and c595 are designated as primary probes herein, they define a shorter DNA segment containing the trait locus than flanking probe r90 or r92.

Additional probes can be identified as equivalent to the probes claimed herein by determining the frequency of recombination between the additional probe and a claimed probe. Such determinations utilize an improved method of orthogonal contrasts based on the method of K. Mather (1931) described in "The Measurement of Linkage in Heredity," Methuen & Co., London, followed by a test of maximum likelihood to determine a recombination frequency (Allard, R. W. (1956) Hilgardia pp. 235–278). If the value of the recombination frequency is less than or equal to 0.10 (i.e. 10%) in any cultivar, then the additional probe is considered equivalent to the claimed probe for purposes of this invention.

DNA segments containing sequences involved in conditioning resistance to the European corn borer (ECB) are also identified. These segments fall between primary probes, flanking and primary probes or between flanking probes.

For purposes of this invention, it is not necessary to identify the chromosome on which each segment occurs, but these locations are provided herein as a matter of general information. The numbers in parentheses below refer to recombination frequencies between the listed markers, and they are expressed as map units. These numbers may vary from cultivar to cultivar and are not part of the essential definition of the DNA segments. The DNA segments of this invention are:

chromosome 4: r115 to UMC31 (23.0); Primary probe= c94 chromosome 4: UMC31 to r109 or c39 (13.4); Primary probe=BNL5.46 chromosome 9: r90 to r92 (14.6); Primary probes=p1000 and c595

A preferred segment on chromosome 9 is:

chromosome 9: p1000 to c595 (9.0); These are both primary probes

The primary and flanking probes of this invention were deposited under the Budapest Treaty with the In Vitro International Depositary, 611 P. Hammonds Ferry Rd., Linthicum, Md. 21090 as deposit no. IVI 10219 on Dec. 12, 1989. The deposit is entitled "Corn (*Zea Mays*) nuclear DNA clones," and comprises c94, BNL5.46, p1000, c595, r115, r109, c39, r90, r92 and UMC31. Probes BNL5.46 and UMC31 are publicly available in addition to having been deposited, and may be obtained from the University of Missouri, Curtis Hall, Columbia, Mo. 65211.

A general method for identifying genetic loci that determine resistance to the ECB is provided. All sources of ECB resistance that have been identified to date are polygenic; that is, the resistance is determined by several genes. Nonetheless, the method provided herein is equally useful for identifying single gene resistance. This method comprises:

(a) Development of a set of recombinant inbred (RI) lines, preferably at least 200, that represents a random mixing of two parental genotypes (see Burr et al. (1988) Genetics 118:519–526 for a discussion of the advantages of RI lines for RFLP mapping; also see C. Wehrhahn and R. W. Allard (1965) Genetics 51:109–119 relative to the use of RI lines in conventional breeding of quantitative traits; and N. M. Cowen (1988) Theor. Appl. Genet. 75:857–862 for a discussion of the use of RI lines in RFLP mapping of quantitative traits). One parent demonstrates a high degree of resistance to the ECB; this is the "donor" parent. The other parent is an elite genotype of maize expressing a highly desirable agronomic phenotype but that is susceptible to the ECB. This susceptible parent may or may not be closely related to the donor parent. The RI set is produced by an initial cross of these two parents, followed by a series of self-pollinations to an inbred state, preferably the F6 generation. Adequate seed of the RI lines should be produced to allow for sufficient, replicated experiments to assess the response of the RI set to ECB infestation.

(b) Analysis of DNA from the parental genotypes and the RI lines with RFLP probes that demonstrate polymorphism at the RFLP-marked alleles in the two parental genotypes. Preferably, RFLP probes are chosen from a previously mapped set of probes to give sufficient representation of the maize genome at evenly spaced intervals. Preferably, sufficient markers will be used to provide intervals along the maize genome of no more than 20 map units. RFLP markers are preferred in this analysis, but a combination of RFLP and other markers may also be employed. Following an initial statistical analysis as described below, additional markers, particularly in those sections of the genome that have been shown to be statistically correlated with the trait, may be used and the method herein described repeated.

As discussed above, the maize genome has also been mapped using publicly available RFLP probes, isozymic and morphological markers. However, the method described herein does not require the use of previously mapped markers. It is possible to develop a set of random RFLP probes, by techniques known to the art, for use in this invention without knowing chromosomal locations.

As described above, RFLP markers are developed by the use of bacterial endonucleases referred to as restriction enzymes. One or more of a large and still increasing number of such restriction enzymes may be used to study the maize genome. Preferably, only one restriction enzyme is used. In the preferred embodiment of this invention, the restriction enzyme is EcoRI.

(c) Evaluation of the parental and RI lines for their response to infestation by the ECB. Preferably, this evaluation is performed for two or more years in succession on all genotypes at several locations that vary in environmental factors which influence the growth of maize. As described above, expression of quantitatively inherited traits such as ECB resistance is often strongly affected by environmental factors. Since this method locates heritable factors in the maize genome, it is important to minimize phenotypic variation due to nonheritable factors. As is known to those skilled in the art, this can be accomplished by evaluating genotypes during two or more growing seasons in a variety of environmental conditions (temperature, soil structure, available moisture, wind, pest incidence, etc.).

A scoring system to assess resistance is employed that can adequately reflect the range of phenotypes that are expressed. In particular, the scoring system should result in a good differential expressed between the two parental genotypes. Preferably, implementation of the scoring system on a random population such as the RI set described in (a) will result in a relatively linear range of phenotypes between the extremes. Guthrie, (1960) Ohio Agricultural Experiment Station Research Bulletin 860, has described a rating scale of 1–9 that satisfies these goals and is used in the preferred embodiment of this invention.

(d) Statistical analysis of the data obtained in (b) using multiple regression by leaps and bounds ("LEAPS") to identify a set of RFLP marker probes ("primary set") that represents the minimum number of markers that account for the maximum percentage of the expression of the trait across locations. The primary set is comprised preferably of only RFLP probes, but it may include other markers. The "LEAPS" analysis also provides information enabling selection of a set of flanking markers that define the boundaries of DNA segments containing the genetic loci conditioning expression of the trait.

Initially, data (including all genotypes) are analyzed separately from each year and each location. Thus, a "site-specific" marker set is identified for each location and year. Site-specific marker sets are compared, and a subset of markers common to all sets is identified.

The statistical analysis is continued by analyzing this subset of markers (i.e., those repeatedly associated with the trait at all locations) by multiple regression, a standard method known to those in the art. This analysis determines the relative contribution of each RFLP marker in the primary set to the overall phenotype. Thus, this method allows a ranking of the RFLP-marked loci according to their contribution to expression of the trait. For efficient use of this marker set in breeding, it is important to identify the fewest number of loci that can account for a maximum percentage of expression of the trait. As is known to those skilled in the art, this method may be repeatedly applied using additional primary and flanking markers to maximize association of the RFLP probes with the trait.

Other statistical analyses of the RFLP data may be employed. For example, the method of "interval mapping" (Lander, E. S. and Botstein, D. (1989) "Mapping Mendelian factors underlying quantitative traits using RFLP linkage maps" Genetics 121:185–199) may be used. This approach has been formalized in a computer program called "MAPMAKER-QTL" developed by S. D. Tanksley and E. S. Lander (see Paterson, A. H. et al. (1988) Nature 335:721–726 for information). Alternatively, a combination of the "LEAPS" method and the "interval mapping" method could be used.

A method for transferring the genetic loci of this invention that condition resistance to the ECB to an elite maize genotype that is susceptible to the ECB is also provided. This method comprises:

(a) Analyzing the DNA of the two parents with a sufficient number of RFLP marker alleles (selected on the basis of the existence of polymorphic alleles between the parents) distributed throughout the maize genome. Included in this group of RFLP markers are the primary and flanking markers associated with loci governing ECB resistance identified as described above. It may be necessary to vary and/or increase the number of restriction enzymes used to assure polymorphism at a sufficient number of the loci associated with resistance to the ECB.

(b) Sexually crossing the two parental genotypes to obtain a progeny population and analyzing those progeny for the presence of (1) RFLP marker alleles associated with ECB resistance, and (2) RFLP marker alleles associated with the recurrent, elite (i.e., recipient) genotype.

(c) backcrossing the individuals of (b) that contain the RFLP alleles associated with ECB resistance to the elite (recipient) genotype to produce the first backcross population, and then continuing a backcrossing program until a final progeny, having the desired similarity to the recipient genotype and resistance to ECB, is obtained. Preferably, selection on individual progeny in the crossing and backcrossing steps is done by RFLP marker analysis at each generation.

EXAMPLES

Example 1

Genetic Stocks and Population Development

The maize (*Zea mays* L.) inbreds DE811 and B73HtHtrhmrhm were used to produce a progeny population of recombinant inbred (RI) lines. DE811 is a yellow dent line released by the University of Delaware Agricultural Experiment Station, and it carries resistance to the first and second generation of the ECB (Hawk, J. A. (1985) Crop Science 25:716). B73HtHtrhmrhm is a dent inbred released by Iowa State University (Ames, Iowa). The designations Ht and rhm represent genes for resistance to the plant pathogenic fungi, *Helminthosporium turcicum* Race 1 and *Drechslera maydis* Race 0, respectively.

Initially, F1 seed was collected from the DE811× B73HtHtrhmrhm cross. An F1 plant was self-pollinated to produce seed of the F2 generation. From the F2 through the F5 generation, four-kernel hill plots were planted with one plant being chosen for advance to the next generation. At the F6 generation, seed was increased and approximately 200 lines were selected, based on adequate seed production for the requirements of replicated field trials and screening. Since no selection was exerted on this population, it is expected that the distribution of genes in each line should have a mean value of 50% from each parent. This was confirmed experimentally by examining the 200 RI lines for the presence of each parental allele at 106 RFLP marker loci. The mean value for the RI population is centered at approximately 50% representation from each genome. The distribution of allele frequencies (where 0=100% DE811 alleles, and 1=100% B73 alleles) for all 106 loci was centered at 0.5. These results confirm that the RI population is a random sample of lines derived from the DE811×B73HtHtrhmrhm cross.

Example 2

Molecular Methods

This invention involves the use of a maize RFLP marker "library" that consists of at least 230 loci identified by proprietary probes and at least 70 loci identified by publicly available markers. These markers are organized in linkage groups that are assigned to each of the ten maize chromosomes. The chromosomal location of these markers is not needed to teach this invention, but it is provided as a matter of general information.

A subset of loci, chosen from those loci identified by RFLP probes in the maize library described above, was used to screen the approximately 200 RI lines used in the field studies. These loci were chosen to give good representation of the maize genome. On average, the "interlocus distance," i.e., the genetic distance between any two loci, was not greater than twenty map units. Following an initial statistical evaluation, additional markers were used to probe those regions of the genome that were found associated with the phenotypic trait of ECB resistance. In total, 106 loci have been analyzed for their association with ECB resistance.

For convenience, these probes are maintained for long-term storage as clones in plasmids that are suitable for use in the Riboprobe system provided by Promega (Madison, Wis). For use in analyzing maize DNA samples, these plasmids are prepared by methods well-known in the art (for example, see Kieser, T. (1984) Plasmid 12:19–36). $^{32}$P-labeled RNA probes were prepared from these plasmids following the specifications of the Promega kit. Specific activities of $0.8–1.2\times10^8$ cpm/μg plasmid DNA were used throughout these studies.

2.1 DNA extraction

Samples were collected for extraction of DNA from the two parental types and each RI line using leaves from seedlings grown in greenhouse flats.

DNA was isolated as follows: crude nuclei were prepared by a modification of Murray, M. G. and Kennard, W. C. (1984), "Altered chromatin conformation of the higher plant gene phaseolin." Biochemistry 23:4225. Nuclei extraction buffer contained 20 mM PIPES (pH 7), 3 mM MgCl$_2$, 0.5M hexylene glycol, 10 mM orthophenanthroline, 10 mM sodium metabisulfite and 200 μM aurintricarboxylic acid. Crude nuclear pellets (500×g, 10 min.) were lysed in 15 mM EDTA, 0.7M NaCl, 0.5% cetyltrimethyl ammonium bromide and 10 μg/ml proteinase K for 1 hour at 65° C. Insoluble material was removed by centrifugation (10,000×g 10 min.) and the DNA precipitated by addition of ammonium acetate and isopropanol to final concentrations of 2.5M and 50% respectively. DNA was dissolved in DNA dialysis buffer containing 2 μg/ml RNAse A and incubated several hours at 37° C. After phenol extraction, the DNA was reprecipitated with isopropanol, rinsed and dissolved in DNA dialysis buffer. DNA concentrations were determined fluorometrically (Murray, M. G. and Paaren, H. E. (1986), "Nucleic acid quantitation by continuous flow fluorimetry," Anal. Biochem. 154:638–642.

2.2 Electrophoresis and Blotting

Five μg of restricted DNA was typically loaded into 2.7 mm wide lanes cast in 0.85% agarose gels made in 100 mM Tris-acetate (pH 8.3) and 2.5 mM EDTA. Electrophoresis was at 2.5 volt/cm for 15–18 hours. Gels were stained for 30 min. in 0.1 μg/ml ethidium bromide prior to photography and UV nicking. A short wave UV dose of 1400 μW/cm² (one min. from one 15 watt germicidal bulb at a distance of 6 cm) was sufficient to introduce 1 nick per 3–4 kb and optimize transfer from the gel. Uv nicking was faster and more easily controlled than acid depurination. The gel was denatured in 150 mM NaOH and 3 mM EDTA for 20 minutes, rinsed briefly in distilled water and neutralized for 20 minutes in 150 mM sodium phosphate buffer (pH 7.8). DNA was transferred onto Genetran 45 or Zetabind membranes by capillary blotting using 25 mM sodium pyrophosphate (pH 9.8) as the transfer buffer. The membranes were soaked for at least 10 minutes in sodium pyrophosphate prior to transfer and dried thoroughly following transfer. Membranes were pretreated for 2 to 3 hours at room temperature in 2% SDS, 0.5% BSA and 1 mM EDTA prior to their first use.

2.3 Blot Hybridization

Blots were prehybridized overnight at room temperature in 100 mM sodium phosphate buffer (NaPB, pH 7.8), 20 mM sodium pyrophosphate (NaPPi), 5 mM EDTA, 1 mM orthophenanthroline, 0.1% SDS, 500 μg/ml heparin sulfate, 10% dextran sulfate, 5 μg/ml poly(C), 50 μg/ml herring sperm DNA. Probe was added to a final concentration of 2–500,000 cpm/ml. It was frequently possible to analyze 2–4 marker loci together on a single blot if the positions of the restriction fragments did not interfere with each other. After 6 hours at 65° C., blots were rinsed briefly in excess wash buffer (25 mM NaPB (pH 8.6), 1.25 mM NaPPi, 0.25 mM EDTA and 0.1% SDS) at 65° C. Blots were then given three 15 minute washes in wash buffer at 65° C. Blots were autoradiographed on Kodak XAR 5 film using one DuPont Cronex Lightning Plus intensifying screen at −80° C.

Example 3

Plant Response to European Corn Borer Infestation 3.1 Experimental Field Design

Fields were set up as a series of ranges. Each range consisted of 66 rows of maize. Three border rows of B73 were planted on each side of the range as well as a buffer zone of B73 at each end, leaving 60 rows per range for data collection. Each row was 21.5 feet long and 30 inches wide, with a 4-foot wide alley between each range. A block of four ranges made up each replication. Thirty-four kernels of maize were planted in each row, and these were thinned to a uniform stand of 29 plants per row, giving an effective population of approximately 24,000 plants per acre.

Within each range, alternate check rows of B73 (ECB-susceptible) and DE811 (ECB-resistant) were inserted every fifth row. Thus, there were 20 susceptible checks, 20 resistant checks and 200 RI lines per replication. Within each replication, the 200 RI lines were randomized with respect to location at each planting site: check rows were always rows 6, 12, 18, 24, 30, 36, 42, 48, 54, and 60.

3.2 Inoculation and Scoring of Damage

Ten plants on one end of each row (skipping the first plant) were infested at the mid-whorl stage with 50 to 60 live larvae of the ECB in two applications of 25 to 30 larvae each, spaced one to two days apart.

The response of each RI line to infestation was evaluated fourteen days after the last infestation according to the standard ECB rating scale originally developed by Guthrie et al. (1960) "Leaf and Sheath Feeding Resistance to the European Corn Borer in Eight Inbred Lines of Dent Corn," Ohio Agricultural Experiment Station Research Bulletin 860, pp. 3–37. In this rating scale, nine classes are identified:

Class 1: No visible leaf injury or a small amount of pin or fine shot-hole type of injury on a few leaves Class 2: Small amount of shot-hole type lesions on a few leaves Class 3: Shot-hole injury common on several leaves Class 4: Several leaves with shot-hole and elongated lesions Class 5: Several leaves with elongated lesions Class 6: Several leaves with elongated lesions (about 1 inch)

Class 7: Long lesions common on about one-half of the leaves

Class 8: Long lesions common on about two-thirds of the leaves

Class 9: Most of the leaves with long lesions

The results of ECB damage scoring for two years are summarized in Table 1. Since these data provided a good differential between the parental lines as well as a relatively linear range of phenotypes between the rating extremes, they validate this rating scheme as an appropriate assessment of the quantitative trait of ECB resistance.

TABLE 1

Field Data on ECB Resistance:
Summary Statistics for Damage Ratings*
Parental Genotypes and RI Lines at 4 Locations

| | Parental Genotypes | | | | | |
|---|---|---|---|---|---|---|
| | DE811 | | B73Htrhm | | RI Lines | |
| Location | Mean | Std dev. | Mean | Std dev. | Mean | Std dev. |
| 1 1988 | 4.6 | (0.7) | 6.4 | (0.8) | 6.0 | (1.3) |
| 1989 | 3.8 | (0.8) | 7.1 | (1.0) | 6.0 | (1.8) |
| 2 1988 | 4.4 | (0.7) | 6.3 | (0.7) | 5.6 | (1.0) |
| 1989 | 3.5 | (0.7) | 7.5 | (0.5) | 5.9 | (1.7) |
| 3 1988 | 3.9 | (0.6) | 7.0 | (0.8) | 5.6 | (1.3) |
| 1989 | N.A. | | N.A. | | N.A. | |
| 4 1988 | 4.1 | (0.4) | 7.4 | (0.9) | 5.7 | (1.3) |
| 1989 | 3.4 | (0.7) | 7.2 | (0.8) | 5.5 | (1.8) |

*Ratings are based on the standard 1–9 scale developed by Guthrie et al. (1960) Ohio Agricultural Experiment Station Research Bulletin 860, pp. 3–37.
N.A. - not available Example 4.1

Determination of Genetic Variance

The observed phenotypic variance for any trait which exhibits continuous variation includes variance due to genetic factors plus variance due to any other cause. The design of this study permitted an analysis of variance due to locations, years, genotypes and the interaction (if any) between locations, years, and genotypes. As shown by Comstock, R. E. and Robinson, H. F. (1952), "Genetic parameters, their estimation and significance," Proc. Sixth International Grasslands Congress, pp. 284–291, this method enables the breeder to estimate that proportion of the variance which is due to genetic factors. The analysis revealed that 85% of the observed phenotypic variance in the population was due to genetic factors.

Example 4.2

Statistical Association of Molecular and Field Data

Statistical analysis was done on a Pyramid model 90X computer using a UNIX environment and "S" statistical software ("S: an interactive environment for data analysis and graphics" (1984) R. A. Becker and J. M. Chambers, Wadworth, Inc.). Data from 1988 were initially analyzed separately for four locations, designated 1–4 in this application. Data for locations 1, 2 and 3 included ratings and DNA RFLP analysis for 200 RI lines. At location 4, phenotypic data were available only for 192 of the 200 RI lines. For 1989 data were available only from locations 1, 2 and 4. A total of 163 RI lines were analyzed at each site.

An analysis of variance (ANOVA) of the field data revealed statistically significant differences in ECB ratings across locations and suggested the presence of genotype by environment (g×e) interactions. Therefore, data for each location were analyzed separately. Subsequently, further analyses were performed using those marker alleles that were consistently associated with resistance to the ECB at all locations.

The initial evaluation followed Mallows' method of multiple regression by leaps and bounds ("LEAPS," see Furnival, G. M. and Wilson, R. W. (1974) "Regression by leaps and bounds." Technometrics 16(4):499–511). This method of analysis is based on algorithms that allow selection of a subset of RFLP markers that account for the most phenotypic variation with the fewest markers, without examining all possible subsets.

It is recognized that the "LEAPS" analysis can be affected by the order in which individual markers are evaluated. This effect has been minimized by performing multiple iterations, with the RFLP marker order randomized for each iteration. Analyses using both 40 and 80 iterations have been performed on these sets of data; no significant difference in the analyses were found. Thus, forty iterations were considered adequate for these data sets to eliminate spurious effects due to the order of analysis.

The results from the "LEAPS" analysis for each location are presented in Tables 2 and 3 for 1988 and 1989, respectively. Inspection of the location-specific marker sets revealed a subset of four RFLP probes that was common across locations and years: c94, BNL5.46 and either p1000 or c595. p1000 and c595 are adjacent markers on chromosome 9.

A standard multiple regression analysis was performed on each location-specific marker set to determine the proportion of the genetic variation in resistance that could be explained by the marker set. Similarly, a multiple regression analysis was also performed for each location using the subset of three RFLP markers that were consistently associated with expression of resistance at every location. The results of these analyses are presented in Tables 2 and 3. Analysis of p1000 and c595 reveals that the effects of these two markers are not additive. Rather, they can be used interchangeably, indicating that the resistance locus is equidistant between the two. The subset of three RFLP markers accounted for 71–92% of the phenotypic variation explained by the location-specific sets. Furthermore, a single locus, marked by c94, has a major influence in conditioning resistance at all locations.

TABLE 2

| | Location 1 | Location 2 | Location 3 | Location 4 |
|---|---|---|---|---|
| A. First Brood European Corn Borer Resistance 1988 Probes Chosen by "Leaps and Bounds" | | | | |
| Chromosome 1 | | | | |
| r77 | | | + | |
| r294a | | + | | |
| c516 | | | + | |
| r175 | | + | | |
| Chromosome 2 | | | | |
| r216a | | | + | |
| UMC8B | | | | + |
| UMC134 | + | + | | |
| Chromosome 3 | | | | |
| UMC121 | | | + | |
| r271 | | | + | |
| Chromosome 4 | | | | |
| c94 * | + | + | + | + |
| UMC31 | | | | + |
| BNL5.46 * | + | + | + | + |
| BNL8.23 | | | | + |
| Chromosome 5 | | | | |
| c563a | | | + | |
| Chromosome 6 | | | | |
| UMC42 | + | + | | |
| Chromosome 8 | | | | |
| UMC124 | | + | | + |
| UMC93 | | | + | |
| Chromosome 9 | | | | |
| r41 | + | + | | |
| BNL7.13 | | | | + |
| r90 | | | + | + |
| p1000* | + | | + | + |
| B. Explained Proportion of Genetic Variance | | | | |
| Location Set | .59 | .61 | .66 | .72 |
| (*) Select Set | .52 | .56 | .47 | .63 |
| c94 | .33 | .36 | .32 | .39 |
| Select Set/ total set (×100%) | 88% | 92% | 71% | 89% |

TABLE 3

| | Location 1 | Location 2 | Location 4 |
|---|---|---|---|
| A. First Brood European Corn Borer Resistance 1989 Probes Chosen by "Leaps and Bounds" | | | |
| Chromosome 1 | | | |
| r294a * | + | | + |
| BNL12.06 | + | | |
| BNL6.32 | + | | |
| Chromosome 2 | | | |
| c939 | | | + |
| UMC134 | + | | |
| Chromosome 3 | | | |
| c936 | | + | + |
| r50a | | + | |
| Chromosome 4 | | | |
| r115 | | + | + |
| c94 * | + | + | + |
| UMC31 | + | | |
| BNL5.46 * | + | + | + |
| Chromosome 5 | | | |
| UMC108 | | + | |
| Chromosome 7 | | | |
| BNL14.07 | + | | |
| Chromosome 9 | | | |
| r41 | | + | |
| P1000 | | + | |
| c595* | + | | + |

TABLE 3-continued

|  | Location 1 | Location 2 | Location 4 |
| --- | --- | --- | --- |
| B. Explained Proportion of Genetic Variance | | | |
| Location Set | .72 | .54 | .59 |
| (*) Select Set | .60 | .45 | .48 |
| c94 | .40 | .32 | .35 |
| Select Set/ total set (×100%) | 84% | 83% | 82% |

Of these four markers, two—BNL5.46 and c94—are located on the short arm of chromosome 4. However, inspection of the location of these markers relative to other markers included in the analysis indicates that these two markers identify two separate loci involved in determining resistance to ECB. This is indicated because a third marker, UMC31, located between c94 and BNL5.46 in this population, is not chosen consistently in the analyses.

We claim:

1. A nucleic acid probe linked to European Corn Borer resistance, selected from the group consisting of c94, having accession no. NRRL B-21845; p1000, having accession no. NRRL B-21847; c595, having accession no. 21846; r115, having accession no. NRRL B-21851; r109, having accession no. 21850; c39, having accession no. 21844; r90, having accession no. 21848; and r92, having accession no. 21849.

2. A nucleic acid probe selected from the group consisting of c94, having accession no. NRRL B-21845; p1000, having accession no. 21847; and c595, having accession no. 21846.

3. A nucleic acid probe of claim 2 in combination with at least one flanking marker probe selected from the group consisting of r115, r109, c39, r90, r92 and UMC31.

4. A set of probes comprising all the probes of claim 1, and additionally comprising UMC31 and BNL5.46.

5. A set of probes comprising all the probes of claim 1.

6. A set of probes comprising all the probes of claim 2.

7. An isolated DNA segment comprising a section of the maize chromosome coding for a factor conditioning resistance to the ECB selected from the group consisting of:

(a) the segment located on the short arm of chromosome 4 lying between (and including) markers r115 and UMC31;

(b) the segment located on the short arm of chromosome 4 lying between (and including) markers UMC31 and r109;

(c) the segment of chromosome 9 lying between (and including) markers p1000 and c595;

(d) the segment of chromosome 9 lying between (and including) markers r90 and r92.

* * * * *